United States Patent [19]

Lemonnier

[11] 4,351,900

[45] Sep. 28, 1982

[54] TEST METHOD AND APPARATUS FOR THE PRESENCE OF MICROORGANISMS IN AMPOULE

[75] Inventor: Jean Lemonnier, Le Vesinet, France

[73] Assignee: Millipore Corporation, Bedford, Mass.

[21] Appl. No.: 229,918

[22] Filed: Jan. 30, 1981

[51] Int. Cl.³ .............................................. C12Q 1/22
[52] U.S. Cl. ...................................... 435/31; 435/30; 435/287; 435/292
[58] Field of Search ...................... 435/31, 30, 29, 34, 435/287, 292

[56] References Cited

U.S. PATENT DOCUMENTS 4,036,698  7/1977  Bush et al. .............................. 435/31
4,292,405  9/1981  Mascoli et al. ....................... 435/31

Primary Examiner—Robert J. Warden
Attorney, Agent, or Firm—Paul J. Cook; David Prashker

[57] ABSTRACT

A method and apparatus for testing the sterility of the dry contents of a sterile ampoule. A dual channel needle is inserted into the container and a dissolving solution is injected into the ampoule to form a solution. A rinsing solution is circulated into the interior of the apparatus to remove that solution which is then directed to means for culturing and incubating a filtrate of the solution to determine whether microorganisms are present therein. The needle is retained by hand into the ampoule and held by the cap of the closed transfer chamber during rinsing.

8 Claims, 3 Drawing Figures

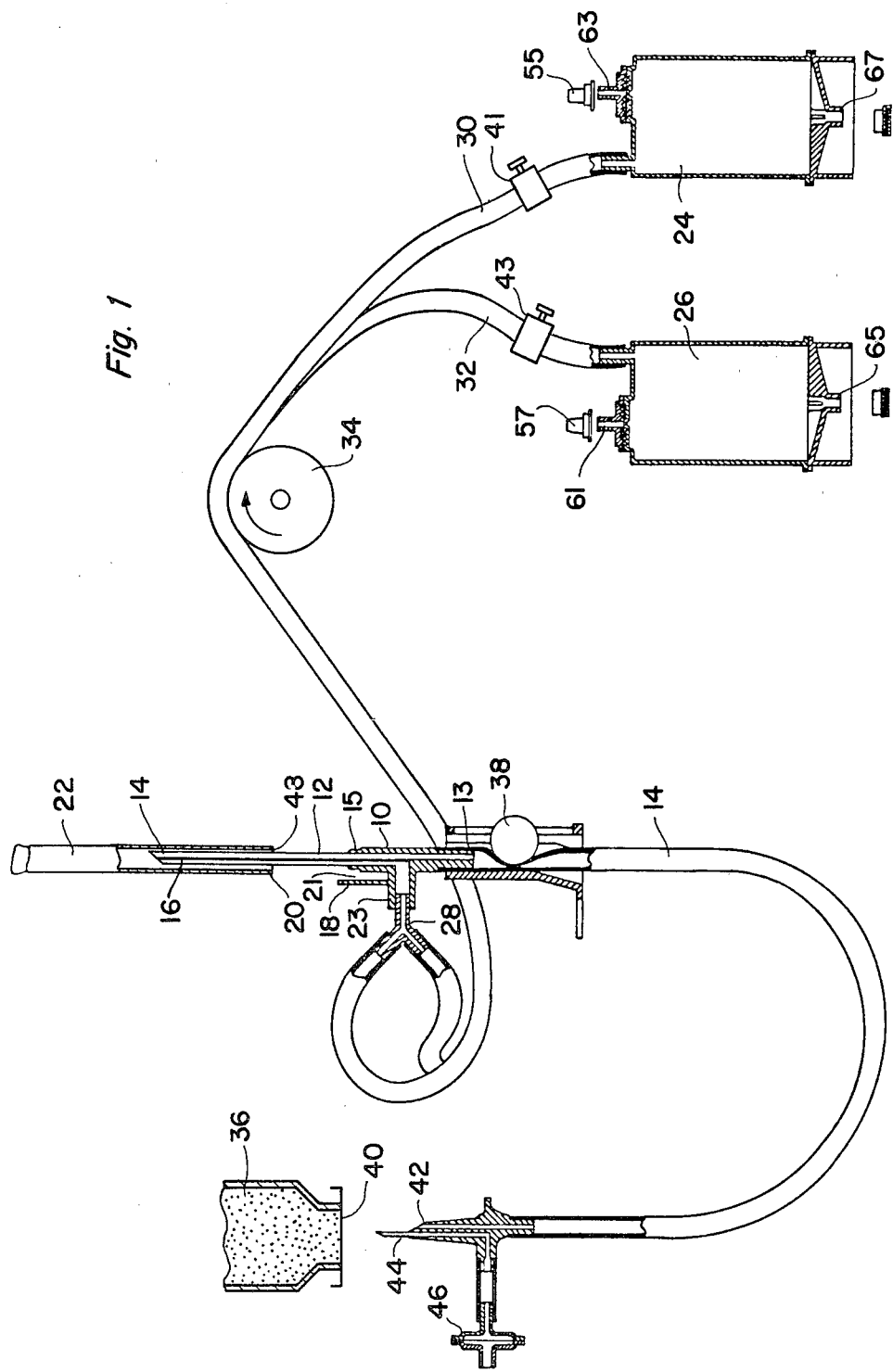

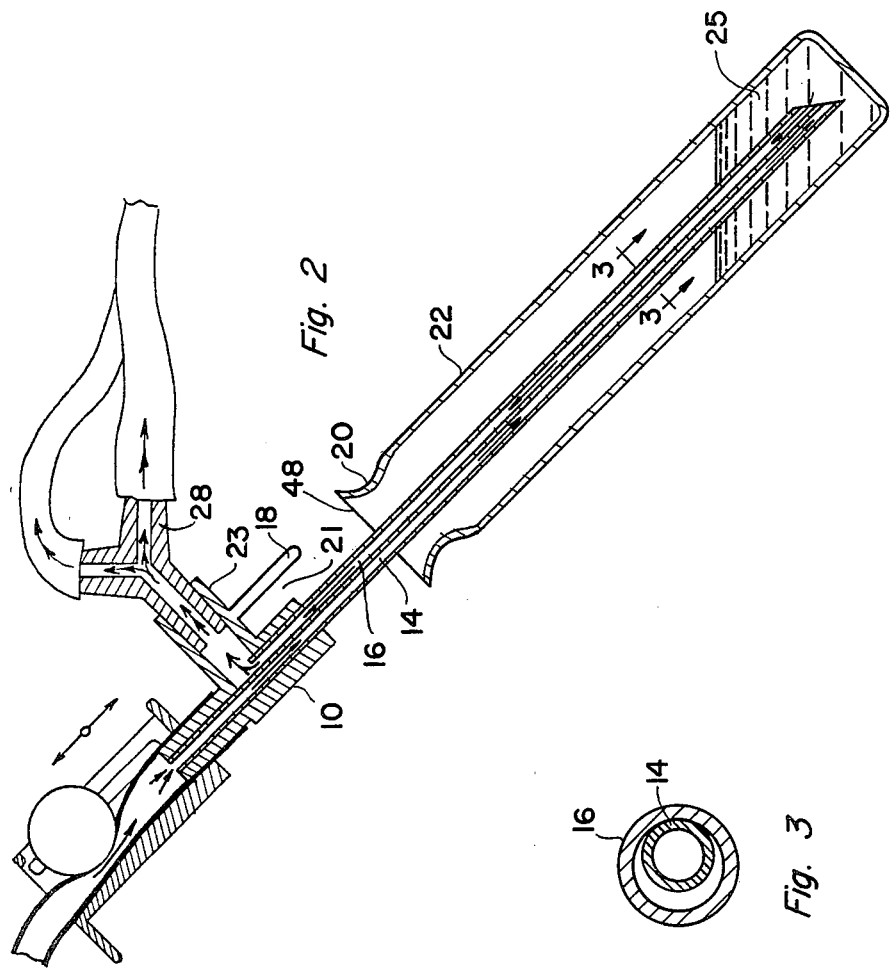

TEST METHOD AND APPARATUS FOR THE PRESENCE OF MICROORGANISMS IN AMPOULE

BACKGROUND OF THE INVENTION

This invention relates to a method and apparatus for testing for the presence of microorganisms.

At the present time, it is necessary to perform sterility tests on samples of pharmacological compositions and apparatus to comply with federal regulations in the United States and similar regulations in other nations.

Any such testing procedure must prevent adventitious microbial growth transmitted to the article or composition being tested or to the substrate containing a test culture medium from the environment; otherwise, the test results are invalid. Therefore, it is necessary to demonstrate that the proper precautions have been taken to exclude extraneous microorganisms throughout the test period.

When testing sterilized dry solids, the dry solid or a suspension or solution of the dry solid is transferred from its container, e.g. ampoule, to a sterile chamber where it is mixed with a growth medium. Prior to the present invention, it was common practice to pour by hand the contents of the ampoule into the sterile chamber, thereby increasing the chances of contamination. The suspension or solution in the sterile chamber then is contacted with a growth medium and incubated. Typically, for bacteria, a thioglycollate medium has been utilized which includes a resayurin additive to provide for color indication, and also agar to inhibit diffusion throughout the medium. A medium which is particularly useful for determining the presence of fungi is soybean-casein digest medium. Another medium which is utilized for this latter purpose is a Sabouraud medium. The presently utilized technique for testing powders requires two week incubation time and increases the risk of hand contamination, thereby causing an excessive number of false positive tests. Obviously, false positive tests are undesirable, for example, since they require resterilization of the entire batch or product which increases the risk of ruining the batch or product.

It would be highly desirable to provide a procedure for testing the powdered contents of an ampoule which eliminates or minimizes the risk of hand contamination during the test procedure.

SUMMARY OF THE INVENTION

In accordance with this invention, the dry contents of an ampoule are tested for sterility using a special adaptor. The adaptor includes a needle having a dual channel. One channel is in fluid communication at one end with a container for a dissolving liquid for the dry composition, a rinsing liquid or a culture medium and at the second end with the interior of the ampoule. The second channel is in fluid communication at one end with the interior of the ampoule and at the other end with a means for filtering the contents of the ampoule under sterile conditions in order to test the liquid for microorganisms.

In operation, the ampoule is open and the dual channel needle is introduced into the very end of the ampoule preferably with the edge of the needle oriented down to the inside wall of the ampoule, and is retained in position to permit dissolving the dry contents or removing the dry contents without being exposed to the surrounding environment. In a first step, the dry contents are dissolved with a liquid and the resultant solution is removed with a sterile liquid to a means for filtering the liquid under sterile conditions so that any microorganisms can be isolated on the filter and can be exposed to a culture medium suitable for growth of a particular class of microorganisms. Dissolution of the dry contents and emptying of the sterile container is repeated, usually about 20 times, to produce a representative sample. After the last has been emptied, the interior of the apparatus has been washed and emptied using the transfer chamber to make a closed bridge between the two channels of the needle and, thereafter, a culture medium is added into the container means for the filter in order to promote growth of microorganisms on the filter.

Any apparatus adapted to permit the practice of sterility testing in accordance with legal regulations can be attached to one end of the exit end of the dual channel needle in accordance with this invention. For example, the apparatus disclosed in U.S. Pat. No. 4,036,698 to Bush and Lemonnier is particularly useful in combination with the present invention. U.S. Pat. No. 4,036,698 is incorporated herein by reference. The apparatus disclosed therein generally comprises a pair of canisters each having two ports at one end and a single port at the opposite end, each capable of being hermatically sealed. One of the two ports at one end is provided with a filter capable of allowing air flow in either direction while screening out microorganisms. A second membrane filter is positioned within the cylinder generally parallel to the end having the two ports and spaced apart from that end. The filters sealed at the side walls of the cylinder so that the test product flows through an unfiltered port into the container passes through the second membrane filter and then out the single port at the opposite end. Microorganism contamination within the test product is trapped on the second membrane filter.

In use, two canisters are connected to the exit opening of the dual channel needle by tube means having a Y-shaped splitter so that approximately equal portions of the liquid output from the tube passes into each canister. The liquid passes into the unfiltered port on the two port end of the canister, through the filter in the canister and out the single port at the opposite end of the canister. The size of the openings in the filter is such as to entrap microorganisms while permitting filtered liquid to pass therethrough. After the number of desired samples has been passed from the ampoules, through the tubes and into the canisters, the sterile solution is introduced into the interior of the apparatus to remove any residues of product material within the ampoule and within the tubing connecting the ampoule and the canisters. After the samples have been passed into the canisters and the apparatus have been suitably rinsed, a culture medium suitable for growth of bacteria is flowed into one canister through the unfiltered port at one end while the single port is capped at the opposite end. The transfer chamber is retained in position on the needle while the sterilizing liquid is introduced into the tube. For the introduction of the culture medium, the filtered port on the canister is open to the air to vent air out of the canister while preventing microorganisms within the canister from being removed therefrom. In the case of bacteria testing with a thioglycollate growth medium, the cap over the filter port is replaced after a sufficient period to allow approximately the upper third of the liquid in the canister to be oxidized, a condition indicated by its turning color such as pink. Thereafter, replacement of the cap seals the canister against further aeration and consequently inhibits any further oxidation of the liquid.

In the final step, the single port at one end of the second canister is capped and the filtered port is uncapped to allow venting while a second culture medium such as soybean-casein digest medium, suitable for promoting fungi growth is flowed into the second canister while preventing flow thereof into the first container. Thereafter, the canisters are capped at all three ports to allow incubation for an appropriate period of time at an appropriate temperature. Visual observation of the color or turbidity of the liquid medium then provides for determination of the presence or absence of contaminant microorganisms in the test product.

BRIEF DESCRIPTION OF THE DRAWINGS

FIG. 1 is a side view showing the apparatus of this invention.

FIG. 2 is a cross sectional view of the apparatus of this invention utilizing a dual needle in use.

FIG. 3 is a cross sectional view taken at line 3—3 of FIG. 2.

DESCRIPTION OF SPECIFIC EMBODIMENTS

Referring to FIG. 1, the apparatus of this invention includes a tube 10 having a needle 12 inserted therein axially. The needle 12 has two channels 14 and 16 (see also FIG. 3), which can communicate by a bridge created by the introduction of the needle inside the seal 69 of the closed transfer chamber 68. A first end 13 of tube 10 is adapted to accommodate a feed tube 14 through which can be fed a sterilizing liquid or a nutrient liquid composition. The finger protector 18 is positioned adjacent to the second end 15 of the tube 10 to accommodate the needle handling, thereby to retain it in a stable position when directing or removing liquid thereto or therefrom. A spout 23 also is provided at the end 15 of tube 10 in order to remove liquid which is passed within channel 16 to be directed to canisters 24 and 26. The Y-shaped stream splitter 28 fits over spout 23 and is connected to conduits 30 and 32 which, in turn, communicate respectively with canisters 24 and 26. Liquid is pumped through tubes 30 and 32 by means of peristaltic pump 34 or by any other suitable pumping means.

Tube 14 can be closed or opened to communication with container 36 by means of clamp 38, which container can contain a dissolving liquid, a sterilizing liquid or a nutrient growth composition. Container 36 includes a seal 40 which can be penetrated by needle 44 when a cap (not shown) is removed. Filter 46 is provided in order to filter pressurized gas to the interior of container 36 which forces liquid therefrom through a second opening 42 into tube 14 and tube 10.

The operation of this invention will be described with reference to FIGS. 1 and 2. In the first step, the needle 12 is introduced through seal 48 into the ampoule 22 the edge of the needle oriented down to the inside wall of the ampoule 22 containing sterilized powder 25 so that lip 20 seats within cavity 21 in a stable position. While clamp 38 is open, container 36 containing a dissolving liquid for powder 25 is positioned onto needle 44 to penetrate seal 40. Pressurized gas is applied through gas filter 46, through needle 44 in order to force liquid from container 36, through opening 42, tubes 14 and needle 14 into ampoule 22. When the powder 25 from all ampoules of the sample is dissolved, container 36 is replaced with a container with sterilized rinsing fluid, the needle 12 is introduced into the seal 69 of the transfer chamber 68 to pass the solution into Y-shaped stream splitter 28 with one aliquot passing through tube 32 into canister 26 and the other aliquot passing through tube 30 into canister 24. The filtered ports 61 and 63 of the two canisters are covered with sealing caps 57 and 55 during this step. Each of the aliquots passes through filters positioned within canisters 24 and 26 and then are emptied through aspirating ports 65 and 67 when caps 53 and 55 are removed. It is convenient to effect filtration of the liquid through the filter and out of the tubes 65 and 67 by means of a vacuum pump or the like (not shown) connected with aspirating tubes 65 and 67. Since a vacuum is utilized, the ports 61 and 63 must be closed to the atmosphere in order to allow the liquid to pass through the canisters 24 and 26. Alternatively, a peristaltic pump 34 can be utilized to act upon tubes 30 and 32 to effect passage of the liquid aliquots through the canisters 24 and 26. After the ampoule 22 is emptied, the contents of a plurality of other ampoules are sequentially emptied in the same manner as described above until a suitable volume of sample liquid has been passed through the filters positioned within canisters 24 and 26. After the last ampoule has been emptied, a sterilizing liquid in container 36 is passed through tubes 14, 10, 30 and 32 in order to completely remove the sample to be tested so that the entire sample is filtered in the manner described above.

After the interior of the apparatus has been washed with a sterilizing liquid, a new container 36 containing a microorganism growth medium is positioned onto needles 44 and 42 while clamp 38 is closed and one of the clamps 41 or 43 is open while the other of clamps 41 or 43 is closed. For example, when it is desired to promote fungi growth, a soybean-casein digest medium can be utilized. A description of the preparation of such a medium is described in U.S. Pharmacopeia XVIII at page 852. The fungi growth-promoting liquid in container 36 then passes through tubes 14, 10 and 32 and into canister 26 when clamp 43 is open and clamp 41 is closed. When utilizing a vacuum pump, the growth medium is flowed into canister 26 through tube 32 when the vacuum pump (not shown) is connected to filtered port 61, thereby providing prevention of the air from canister 26 without the possibility of introducing any bacterial contamination through this vent. During introduction of this growth medium, port 65 is closed.

After the introduction of the first growth medium into canister 26, the clamp 43 is closed and clamp 41 is open and a vacuum pump (not shown) is connected to filtered port 63 of canister 24. A new container 36 containing a second microorganism growth medium such as one particularly suitable for promoting growth of bacteria is placed over needle 44 for delivery to canister 24. Typical bacteria growth medium suitable for this purpose comprises a thioglycollate solution, the formulation of which is described in the U.S. Pharmacopeia XVIII at page 852. The canister 24 is filled with this medium and, after being filled, the port 63 is left open to vent air into the canister for a sufficient period to allow the upper one third of the thioglycollate medium to become oxidized as indicated by its turning pink. After one third of the liquid has become pink, a sealing cap is placed over the port 63 to prevent further oxidation.

In the final step, both canisters 24 and 26 are incubated for a period of 7 days with the canister 24 being sealed at all entry ports to prevent any further oxidation of the medium. The thioglycollate medium is maintained at a temperature of 30°-35° C., while the soybean-casein digest medium is maintained at a temperature between about 20° and 25° C. When, at the end of this period, no turbidity is observed in the solution, the product material is deemed to be free from the contaminant microorganism.

As in any sterility test system, control is run in which a sterile control liquid is substituted for the test product in the entire procedure including the medium and processed in the same fashion as the actual material to be tested. If at the conclusion of the incubation period, microorganism growth has been observed in either of the canisters, a review of the details of the procedure must be carried out to ascertain the source of the contamination. Upon conclusion of the procedure, the canisters 24 and 26 may be disposed of in any suitable manner since they can be made of relatively inexpensive plastic materials.

I claim:

1. Apparatus for testing the sterility of the dry contents of a container which comprises a tubular member, a spout positioned at an intermediate point along said tubular member, a needle having a first channel and a second channel, said first channel being longer than said second channel, said needle being positioned within said tubular member to provide fluid communication through said tubular member through said first channel into said container and said second channel positioned to provide fluid communication from said container to said spout.

2. The apparatus of claim 1 including means attached to said spout for stably positioning said container axially with said dual channel needle.

3. The apparatus of claim 1 including means to direct liquid from said spout to a plurality of sterile containers, each of said sterile containers including filter means for filtering microorganisms from said liquid.

4. The process for testing the sterility of the dry contents of a container having a seal which comprises penetrating the seal with a dual channel needle, said needle being positioned within a tubular member having a spout communicating with the interior of said tubular member, passing a liquid capable of dissolving said dry contents through a first channel of said needle to form a solution within said container, passing a sterile rinsing solution through said first channel thereby to force said solution through a second channel of said needle and through said spout, passing said solution from said spout through a filter under sterile conditions, contacting said filter with a growth medium incubating said growth medium and filtered material under sterile conditions and observing the extent of growth on said medium.

5. The process of claim 4 wherein said growth medium is a thioglycollate solution.

6. The process of claim 4 wherein said growth medium is soybean-casein digest medium.

7. The process of claim 4 wherein said growth medium is a Sabouraud medium.

8. The process of claim 4 wherein said liquid exiting from said spout is formed into aliquots and wherein each aliquot is passed through a separate filter under sterile conditions and each of said filters is contacted with a growth medium and incubated.

* * * * *